United States Patent
Whitehead (10) Patent No.: US 12,018,158 B2
(45) Date of Patent: Jun. 25, 2024

(54) NANOPARTICLE DISPERSIONS AND METHODS OF FORMING

(71) Applicant: Sun Chemical B.V., Weeso (NL)

(72) Inventor: Ian Michael Whitehead, Lens (CH)

(73) Assignee: SUN CHEMICAL B.V., Weesp (NL)

( * ) Notice: Subject to any disclaimer, the term of this patent is extended or adjusted under 35 U.S.C. 154(b) by 1039 days.

(21) Appl. No.: 16/757,446

(22) PCT Filed: Dec. 20, 2018

(86) PCT No.: PCT/GB2018/053716
§ 371 (c)(1),
(2) Date: Apr. 20, 2020

(87) PCT Pub. No.: WO2019/122894
PCT Pub. Date: Jun. 27, 2019

(65) Prior Publication Data
US 2021/0189138 A1 Jun. 24, 2021

(30) Foreign Application Priority Data
Dec. 22, 2017 (GB) ..................... 1721808

(51) Int. Cl.
*A61K 8/04* (2006.01)
*B01F 25/313* (2022.01)
(Continued)

(52) U.S. Cl.
CPC ............ *C09B 67/0091* (2013.01); *A61K 8/04* (2013.01); *B01F 25/3133* (2022.01);
(Continued)

(58) Field of Classification Search
CPC ..................................................... A61K 8/04
See application file for complete search history.

(56) References Cited

U.S. PATENT DOCUMENTS 7,323,046 B1    1/2008  Wolf et al.
7,537,654 B1    5/2009  Gaynor et al.
(Continued)

FOREIGN PATENT DOCUMENTS

CN        1917936      2/2007
CN       101796143     8/2010
(Continued)

OTHER PUBLICATIONS

Japanese Office Action for Japanese Patent Application 2020-532649, dated Nov. 22, 2022, (11 pages).
(Continued)

*Primary Examiner* — Benjamin J Packard
(74) *Attorney, Agent, or Firm* — Luke Sande (57) ABSTRACT

A method for preparing a dispersion of nanoparticles of a solid organic dye or pigment in a liquid carrier, and dispersions formed by such a method. The method includes continuously mixing: at least one solution or slurry containing a reactant precursor for the solid organic dye or pigment in an organic or other solvent with the liquid carrier in a counter current mixing reactor to obtain reaction of the reactant precursor and formation of the solid organic dye or pigment as a dispersion of nanoparticles in the liquid carrier and solvent mixture; optionally, removing unreacted reactant precursor and/or by-product from the dispersion when present; and optionally, concentrating the dispersion.

10 Claims, 5 Drawing Sheets

(51) Int. Cl.
*C09B 67/46* (2006.01)
*C09D 11/033* (2014.01)
*C09D 11/037* (2014.01)
*C09D 11/322* (2014.01)
*C09D 11/328* (2014.01)
*C09D 17/00* (2006.01)
*B01F 25/00* (2022.01)
*B01F 101/21* (2022.01)
*B01F 101/35* (2022.01)

(52) U.S. Cl.
CPC .......... *C09D 11/033* (2013.01); *C09D 11/037* (2013.01); *C09D 11/322* (2013.01); *C09D 11/328* (2013.01); *C09D 17/001* (2013.01); *C09D 17/003* (2013.01); *A61K 2800/43* (2013.01); *B01F 2025/918* (2022.01); *B01F 2101/21* (2022.01); *B01F 2101/35* (2022.01); *B01F 2215/0431* (2013.01)

(56) References Cited

U.S. PATENT DOCUMENTS

| | | |
|---|---|---|
| 7,563,318 B1 | 7/2009 | Faucher et al. |
| 7,857,901 B2 | 12/2010 | Carlini et al. |
| 2010/0326321 A1 | 12/2010 | Enomura |

FOREIGN PATENT DOCUMENTS

| | | | |
|---|---|---|---|
| CN | 111566167 | 8/2020 | |
| EP | 1516896 A1 * | 3/2005 | .......... B01F 13/0059 |
| EP | 2184109 A1 | 12/2010 | |
| EP | 2489702 | 8/2012 | |
| JP | 0953035 | 2/1997 | |
| JP | 0953036 | 2/1997 | |
| JP | 2008150558 | 7/2008 | |
| JP | 2008201960 | 9/2008 | |
| JP | 2009-82902 | 4/2009 | |
| JP | 2010511747 | 4/2010 | |
| JP | 2011012214 | 1/2011 | |
| JP | 2012097167 | 5/2012 | |
| JP | 2016160124 | 9/2016 | |
| JP | 2016538995 | 12/2016 | |
| TW | 200920794 | 5/2009 | |

OTHER PUBLICATIONS

International Search Report/Written Opinion for International Application No. PCT/GB2018/053716, dated Apr. 4, 2019, (23 pages).
Chinese Office Action (English/Chinese) for Chinese Application No. 2018800736416, 20 pages.
Japanese Office Action (English/Japanese) for Japanese Application No. 2020-532649, 11 pages.

* cited by examiner

NANOPARTICLE DISPERSIONS AND METHODS OF FORMING

CROSS REFERENCE TO RELATED APPLICATIONS

This application claims the benefit of PCT/GB2018/053716 filed Dec. 20, 2018, having a priority claim to British patent application number GB 17 21808.2, filed Dec. 22, 2017. The contents of these prior patent documents are incorporated herein by reference.

The present invention is concerned with a method for preparing nanoparticle dispersions of solid organic dyes or pigments in a liquid carrier, such as an aqueous based liquid carrier, and with nanoparticle dispersions of solid organic dyes and pigments obtained by the method.

The nanoparticle dispersions may be used as ink concentrates for digital inkjet printing or as cosmetic pastes.

BACKGROUND OF THE INVENTION

The production of ink concentrates suitable for digital inkjet printing presently requires milling of solid pigments or dyes to a suitable nanoparticle size and subsequent dispersion of the nanoparticles in a suitable carrier liquid together with stabilisers, such as wetting agent and/or dispersant.

The production process is a batch process which is often time consuming and costly not least because the required milling is generally protracted and consumes a great deal of energy and large amounts of water and organic solvent.

Furthermore, it is often accompanied by significant problems in reproducibility of the dispersion and the inkjet ink and is limited by the fact that certain pigments or dyes (for example, Disperse Red 55) cannot easily be milled by standard processes to provide stable dispersions.

BRIEF DESCRIPTION OF THE INVENTION

The present invention generally seeks to improve upon this situation by providing a method for synthesis and dispersion of nanoparticles of solid organic dyes or pigments.

The present invention also seeks to provide a method for continuous synthesis and dispersion of nanoparticles of solid organic dyes or pigments.

Accordingly, in a first aspect, the present invention provides a method for preparing a dispersion of nanoparticles of a solid organic dye or pigment in a liquid carrier, the method comprising continuously mixing:

at least one solution or slurry containing a reactant precursor for the solid organic dye or pigment in an organic or other solvent with the liquid carrier in a counter current or concurrent mixing reactor whereby to obtain reaction of the reactant precursor and formation of the solid organic dye or pigment as a dispersion of nanoparticles in the liquid carrier and solvent mixture.

The method may further comprise removing unreacted reactant precursor and/or by-product from the dispersion when present; and optionally, concentrating the dispersion.

Note that references herein to dispersions of a solid organic dye or pigment are references to dispersions of nanoparticles largely comprising the solid organic dye or pigment and having an average particle size below 500 nm.

The nanoparticles may consist essentially of the solid organic dye or pigment in the liquid carrier. Alternatively, the nanoparticles may consist essentially of the solid organic dye or pigment and a wetting agent encapsulating, at least in part, the nanoparticles.

References to a solid organic dye or pigment are references to a synthetic or naturally occurring organic dye or organic pigment which comprises an organic or organometallic molecule and is generally solid at standard temperature and pressure.

The solid organic dye or pigment may be a crystalline solid, colloidal solid (such as a quantum dot) or an amorphous solid.

The method is not limited to any particular class of organic dye or pigment—it being sufficient that the reactant precursor or reactant precursors for the solid organic dye or pigment has some solubility in the organic or other solvent at a suitable temperature and pressure.

The solid organic dye or pigment may, for example, comprise a small organic molecule based on elements such as hydrogen, nitrogen, oxygen, phosphorus and sulphur and the like, combined with carbon. The small organic molecule may also comprise an inorganic metal or metal ion, such as copper (II) ion.

The solid organic dye or pigment may be a hybrid compound in which one or more of a simple organic compound has become attached to an inorganic entity. It may, for example, comprise a lake pigment or a functionalised quantum dot.

In some embodiments, the solid organic dye or pigment has a molecular weight less than or equal to 1500 gmol$^{-1}$, for example, less than or equal to 1200 gmol$^{-1}$, 1000 gmol$^{-1}$ or 850 gmol$^{-1}$.

References to a liquid carrier are references to a liquid in which the solid organic dye or pigment is generally insoluble at standard room temperature and pressure.

In most embodiments, but not in all, the liquid carrier will be different to the solvent used for the at least one solution or slurry of reactant precursor.

The organic or other solvent and the liquid carrier may, therefore, be considered as respectively a solvent for the reactant precursor and an anti-solvent for the solid organic dye or pigment. The liquid carrier of the solvent mixture will normally be present in an amount in excess of the organic or other solvent.

Of course, the organic or other solvent and the liquid carrier should be miscible with each other.

In one embodiment, the mixing of the at least one solution or slurry containing a reactant precursor comprises mixing a solution or slurry of a single reactant precursor for the solid organic dye or pigment in an organic or other solvent with the liquid carrier. In this embodiment, the solid organic dye or pigment is formed by dimerization or oligomerisation of the single reactant precursor.

In another embodiment, the mixing of the at least one solution or slurry containing a reactant precursor comprises mixing a first solution or slurry of a first reactant precursor for the solid organic dye or pigment in an organic or other solvent and a second solution of a second reactant precursor for the solid organic dye or pigment in an organic or other solvent, with the liquid carrier.

In a further embodiment, the mixing of the at least one solution or slurry containing a reactant precursor comprises mixing a first solution or slurry of a first reactant precursor for the solid organic dye or pigment in an organic or other solvent with a liquid carrier containing a second reactant precursor for the solid organic dye or pigment.

In these embodiments, any of the first solution or slurry, the second solution or slurry and the liquid carrier may contain an additional reactant precursor or a reagent such as an acid, base or other catalyst for catalysing the reaction of the reactant precursor or precursors.

Note that the liquid carrier need not contain a reactant precursor or even a reagent such as an acid, base or other catalyst—although it is advantageous that it does because the need for adaptation of existing counter current and concurrent mixing reactors may be avoided.

Suitable counter current mixing reactors include those described in the literature as continuous hydrothermal flow synthesis (CHFS) reactors and used for the synthesis of metals or metal oxides.

The counter current mixing reactors generally comprise an inlet for a first solution, an inlet for a second solution and an outlet for both the first and second solution.

Although the counter current mixing reactor may comprise a T-shaped or Y-shaped reactor, it is preferred that it comprises a reactor in which the second inlet is diametrically opposed to the first inlet and is disposed in the outlet.

Preferred counter current mixing reactors are described, for example, in International Patent Applications WO 2005/077505 A2, WO 2014/111703 A2 and WO 2015/075439 A1 (all of which are incorporated in their entirety by reference herein).

The counter current mixing reactor may, therefore, have a vertical configuration in which the first inlet, the second inlet and the outlet are co-axially disposed. The second inlet may comprise a shaped nozzle, in particular, a conical funnel.

The reactor may also be provided with a preheater for heating one of the solution and liquid carrier and a cooler for cooling the other of the solution and liquid carrier.

Note that it is the intimate mixing of the at least one solution or slurry of a reactant precursor with the liquid carrier in the reactor that leads to reaction of the reactant precursor or precursors to form the solid organic dye or pigment and to the precipitation of nanoparticles of the solid organic dye or pigment in the liquid carrier and solvent mixture.

Suitable counter current mixing reactors also include those adapted from the counter current mixing reactors mentioned above to accommodate mixing of two or more solutions or slurries each containing reactant precursor with the liquid carrier.

One adaptation of the reactor described in International Patent Application WO 2005/077505 A2 provides separate channels within the first inlet or the second inlet or within both inlets.

Another adaptation provides a first inlet and a third inlet which is co-axial with the first inlet so that the first inlet and the third inlet are diametrically opposed to the second inlet.

In one embodiment, a first solution or slurry of a first reactant precursor for the solid organic dye or pigment in an organic or other solvent and a second solution or slurry of a second reactant precursor for the solid organic dye or pigment in an organic or other solvent may be pumped upwards through respective channels in a first inlet and the liquid carrier fed downwards through the second inlet.

Of course, other arrangements are possible albeit that the number of separate solutions of reactant precursors may be limited by practical considerations relating to the adaptation of the inlets of, or the number of inlets to, the reactor.

Note that the concentration of reactant precursor or precursors in the or each solution or slurry or in the liquid carrier may be chosen with respective flow rates to optimise the amounts of the reactant precursor or precursors entering the mixing zone within the reactor for, or towards, complete reaction.

The method may comprise forming one or each solution or slurry containing a reactant precursor containing a wetting agent and/or dispersant provided that it does not interfere with the reaction of reactant precursor or precursors. Alternatively, or additionally, the method may comprise mixing the or each solution or slurry with a liquid carrier containing a wetting agent and/or a dispersant provided that it does not interfere with reaction of the reactant precursor or precursors.

The inclusion of a wetting agent in the organic or other solvent and/or the liquid carrier may provide, at least in part, for encapsulation of nanoparticles of the solid organic dye or pigment as soon as they are formed in the counter current mixing reactor.

The addition of a dispersant to the liquid carrier and solvent mixture may facilitate the encapsulation of the nanoparticles of the solid organic dye or pigment—and may be carried out prior to, or after, removing unreacted reactant precursor or precursors and by-products (if necessary) and, optionally, the organic or other solvent from the mixture.

In one embodiment, the method provides that the liquid carrier contains only a wetting agent and the method further comprises adding a dispersant to the nanoparticle dispersion after removing unreacted reactant precursor or precursors and/or by-products and, optionally, the organic or other solvent from the mixture.

The method surprisingly provides for nanoparticle dispersions of solid organic dyes and pigments which are stable (even without the inclusion or addition of wetting agent and/or dispersant) and well-suited to the production of ink concentrates for inkjet printing.

First, the dispersions are unimodal and show fairly narrow nanoparticle size distribution around a central peak and a mean diameter between 1 nm and 500 nm, in particular, between 100 nm and 300 nm, and, for example, around 120 nm.

Secondly, the dispersions may show median $D_v50$ values between 100 nm and 300 nm and, in particular, around 120 nm. The dispersions may alternatively show $D_v97$ values between 100 nm and 300 nm and, in particular, around 120 nm.

In preferred embodiments, the method comprises forming a solution of a reactant precursor for the solid organic dye or pigment in organic solvent. In these and other embodiments, the liquid carrier may be water or an aqueous based liquid carrier.

In other embodiments, the method comprises forming a solution or slurry of a reactant precursor for the solid organic dye or pigment in water or an aqueous based liquid carrier. In these embodiments, the other solvent is water and the liquid carrier may be an organic solvent, for example, methanol.

Note that in some embodiments, the method provides stable dispersions which do not contain a wetting agent or a dispersant at all or contain only a wetting agent or a dispersant. By contrast, a method relying upon dispersion of a milled solid organic dye or pigment generally requires both a wetting agent and a dispersant.

In other embodiments, the method provides dispersions wherein the amount of the wetting agent and/or the dispersant is substantially different to the amounts used to prepare similar dispersions following milling.

Note that the method does not require that the density of the one or more solution or slurry to be different to that of the liquid carrier—but the organic or other solvent should be miscible with the liquid carrier.

Nor does it require a solution or slurry or a liquid carrier in its near critical or supercritical state. The method may use, however, a liquid carrier, for example comprising water, in its near critical or supercritical state.

The median (or Z) diameter size of the nanoparticles of the solid organic dye or pigment and the stability of the dispersions may be controlled not just by timely use of wetting agent and/or dispersant but also by selection in one or more process parameters.

These process parameters may include the concentration of reactant precursor or precursors in the or each solution or slurry or in the liquid carrier, the temperature and pressure of the or each solution or slurry and/or the liquid carrier, the residence times of the or each solution or slurry and/or the liquid carrier, and the ratio of the flow rates of the or each solution or slurry and the liquid carrier in the reactor.

The temperature at which the method may be carried out may range between room temperature and 450° C. It may, for example, be between room temperature and 250° C., 150° C. or 100° C. The pressure may range between about 0.1 MPa (1 atm) and 25.0 MPa (250 atm). It may be, for example, less than about 20.0 MPa (200 atm) or 10 MPa (100 atm) or even less than about 2.0 MPa (20 atm) or 1.0 MPa (10 atm).

The residence times of the solution or slurry and the liquid carrier in the reactor may, for example, range between 1 second and 5 minutes and the ratio of flow rates may, for example, range between 1:1 and 1:100.

The selection may also control the polydispersity of the nanoparticle dispersion.

In preferred embodiments, the method provides nanoparticle dispersions of the solid organic dye or pigment having unimodal polydispersity. The dynamic light scattering (DLS) poly-dispersity index may range between 0.1 and 3.0, and may be, for example, 2.0 or less, or 1.0 or less.

The method is particularly suitable for, but not limited to, the preparation of dispersions of organic pigments or organic dyes which are insoluble in organic solvents (as well as the liquid carrier) because the reactant precursors are generally soluble in such solvents.

Note, however, that the selection of the reactant precursors will generally take into consideration the likelihood of unwanted chemical reactions, such as hydrolysis, with the liquid carrier to be used.

In a preferred embodiment, the reactant precursors are generally be chosen so that they are soluble in an organic solvent and the organic pigment or organic dye is insoluble in a liquid carrier, such as water.

The method may provide nanoparticle dispersions of solid organic pigments including, but not limited to, substituted and unsubstituted phthalocyanines and, in particular, phthalocyanine blue BN, phthalocyanine green G, pigment blue 15:3, pigment violet 23, pigment yellow 10, pigment yellow 12, pigment yellow 13, pigment yellow 16, pigment yellow 33, pigment yellow 81, pigment yellow 83, pigment yellow 110, pigment yellow 139, pigment yellow 155, pigment yellow 180, pigment yellow 185, pigment red 122, pigment red 208, pigment red 254, pigment green 36, quinoline yellow and quinacridone and mixtures thereof.

The method may provide nanoparticle dispersions of solid organic dyes including, but not limited to, disperse dyes such as Disperse Blue 14, Disperse Blue 19, Disperse Blue 72, Disperse Blue 334, Disperse Blue 359, Disperse Blue 360, Disperse Brown 27, Disperse Orange 25, Disperse Yellow 54, Disperse Yellow 64, Disperse Yellow 82, Disperse Red 55, Disperse Red 60, Macrolex Red H, Disperse Violet 28, Solvent Blue 67, Solvent Blue 70, Solvent Red 49, Solvent Red 160, Solvent Yellow 162, Solvent Violet 10, Solvent Black 29, Vat Red 41 and mixtures thereof.

The organic or other solvent for the or each solution or slurry may be a liquid or gas solvent. It may, in particular, comprise any suitable organic solvent including, but not limited to, ethyl acetate, ethanol, methanol, diethyl ether, tetrahydrofuran, dimethylformamide, dimethyl sulfoxide, N-methyl-2-pyrrolidone, acetone, isopropyl alcohol and mixtures thereof. It may alternatively comprise any suitable gas, and in particular, supercritical carbon dioxide.

The liquid carrier may be an aqueous based liquid carrier or water. The aqueous based liquid carrier may comprise water and one or more of a polyol, such as ethylene glycol, propylene glycol or a polyol having at least 5 carbon atoms, such as those described in International Patent Application WO 2014/127050 A1.

Alternatively, the other solvent may be water or an aqueous based liquid carrier as described above and the liquid carrier may be an organic solvent as described above.

The wetting agent and/or dispersant may comprise one or more water soluble surfactant. The water soluble surfactant may be an anionic surfactant or a non-ionic surfactant which is conventional to the manufacture of dye or pigment dispersions by milling.

Suitable anionic surfactants include, but are not limited to, alkyl sulfates, alkyl ether sulfates, alkyl aryl sulfonates (for example, a linear alkyl benzene sulfonate), α-olefin sulfonates, alkali metal or ammonium salts of alkyl sulfates, alkali metal or ammonium salts of alkyl ether sulfates, alkyl phosphates, silicone phosphates, alkyl glycerol sulfonates, alkyl sulfosuccinates, alkyl taurates, alkyl sarcosinates, acyl sarcosinates, sulfoacetates, alkyl phosphate esters, monoalkyl maleates, acyl isothionates, alkyl carboxylates, phosphate esters, sulfosuccinates, lignosulfonates and combinations thereof. Other suitable anionic surfactants include sodium lauryl sulfate, sodium lauryl ether sulfate, ammonium lauryl sulfosuccinate, ammonium lauryl sulfate, ammonium lauryl ether sulfate, sodium dodecylbenzene sulfate, triethanolamine dodecylbenzene sulfate, sodium cocoyl isothionate, sodium lauroyl isothionate and sodium N-lauryl sarcosinate.

Suitable non-ionic surfactants include, but are not limited to, mono- and di-alkanolamides, amine oxides, alkyl polyglucosides, ethoxylated silicones, ethoxylated alcohols, ethoxylated carboxylic acids, ethoxylated fatty acids, ethoxylated amines, ethoxylated amides, ethoxylated alkylolamides, ethoxylated alkylphenols, ethoxylated glyceryl esters, ethoxylated sorbitan esters, ethoxylated phosphate esters, block copolymers (for example, polyethylene glycol-polypropylene glycol block copolymers), glycol stearate, glyceryl stearate and combinations thereof.

The removal of unreacted reactant precursor or precursors and/or by-products (if necessary) from the dispersion will generally take place outside of the reactor. It may use any suitable method including, but not limited to, washing out, solvent extraction, dialysis, microfiltration, ultrafiltration and ion-exchange chromatography.

In one embodiment, the removal of unreacted precursor and/or by-product comprises washing out with an aqueous solution of a base such as sodium hydroxide followed by washing out with water.

The concentrating step of the method may remove only the organic or other solvent from the dispersion. Alternatively, it may remove the organic solvent together with some of the liquid carrier.

In preferred embodiments, the method further comprises concentrating the dispersion by removing at least the organic solvent from the dispersion.

The concentrating step may be carried out by any suitable method including evaporation, such as rotary evaporation under vacuum or a partial vacuum. In that case, the removal of the organic or other solvent may be carried out at a first temperature and the removal of liquid carrier may be carried out at a second temperature higher than the first.

Of course, the concentrating step of the method may comprise complete centrifugation or filtration and resuspension of the solids in the liquid carrier.

The method may provide a nanoparticle dispersion of solid organic dye or pigment which can be directly used as an ink concentrate for inkjet printing. In that case, the method comprises the removal of unreacted precursor and/or by-product (if present) and removal of at least the organic solvent from the dispersion.

The method may provide a nanoparticle dispersion in which the solid content (viz. the concentration of the bare or encapsulated solid organic dye or pigment) is greater than 3 wt/wt % and less than or equal to 20 wt/wt %. In that case, the method may require concentrating the dispersion.

The solid content of the nanoparticle dispersion may, in particular, range from 5 wt/wt % to 20 wt/wt %, for example, from 5 wt/wt % to 15 wt/wt % or greater than 10 wt/wt % and less than 20 wt/wt % or 15 wt/wt %.

Further, the nanoparticle dispersion may have a concentration of wetting agent between 0.5 wt/wt % and 5.0 wt/wt %, for example, between 0.5 wt/wt % and 3.0 wt/wt %. When present, the concentration of dispersant in the dispersion may range from 0.5 wt/wt % to 5.0 wt/wt %, for example from 0.5 wt/wt % to 3.0 wt/wt %.

In one embodiment, the method provides a dispersion of nanoparticles of a lake pigment. In this embodiment, the method may comprise continuously mixing a first solution or slurry of a first reactant precursor for the solid organic compound in an organic or other solvent with a liquid carrier containing a second reactant precursor for the solid organic compound.

It may, in particular, comprise continuously mixing an organic dye in an organic solvent with a liquid carrier comprising a solution of aluminium sulphate ($Al_2(SO_3)_2$) and sodium carbonate ($Na_2CO_3$).

Note that the nanoparticles will have an average or median diameter ($D_v50$) several orders of magnitude lower than that of particles of lake dyes prepared by other methods. Accordingly, the present method may enable dye loading in the lake pigment which is considerably higher, for example, up to two or three times higher (for example between 40 wt/wt % and 60 wt/wt %) than the maximum loading possible (for example, 20 wt/wt %) by other methods.

In a second aspect, the present invention provides a method for obtaining nanoparticles of a solid organic dye or pigment, comprising continuously mixing:

at least one solution or slurry containing a reactant precursor for the solid organic dye or pigment in an organic or other solvent with the liquid carrier in a counter current or concurrent mixing reactor whereby to obtain reaction of the reactant precursor and formation of the solid organic dye or pigment as a dispersion of nanoparticles in the liquid carrier and solvent mixture; and removing the nanoparticles from the dispersion.

The nanoparticles may be removed from a dispersion containing unreacted reactant precursor or precursors and/or by-product. Alternatively, it can be removed from a dispersion from which unreacted reactant precursor or precursors and/or by-product have been removed.

In a third aspect, the present invention provides a dispersion of nanoparticles of a solid organic dye or pigment in a liquid carrier obtained or obtainable according to the first aspect of the invention.

In a fourth aspect, the present invention provides a dispersion of nanoparticles of a solid organic dye or pigment in a liquid carrier, wherein the nanoparticles consist essentially of the solid organic dye or pigment.

In a fifth aspect, the present invention provides a dispersion of nanoparticles of a solid organic dye or pigment in a liquid carrier, wherein the nanoparticles consist essentially of the solid organic dye or pigment encapsulated, at least in part, by a wetting agent and/or a dispersant.

In one embodiment, the dispersion may comprise a wetting agent and less than 5 wt/wt % of a dispersant.

In any case, the dispersion may have a solids content of the solid organic dye or pigment greater than 3 wt/wt % and less than 20 wt/wt %. The liquid carrier may be an aqueous based carrier. The dispersions may be stable at standard room temperature and pressure for longer than six months. The dispersions may be unimodal (as opposed to those obtained by milling). The dispersions may even comprise a solid organic dye or pigment (such as Disperse Red 55) that cannot be milled to a particle diameter below 500 nm.

In a sixth aspect, the present invention provides an ink concentrate for digital inkjet printing, comprising the dispersion of the fourth or fifth aspect of the invention.

In an eighth aspect, the present invention provides a cosmetic paste, comprising the dispersion of the fourth or fifth aspect of the invention.

Other aspects and embodiments of the present invention will be apparent from those described in relation to the embodiments described in relation to the first aspect.

BRIEF DESCRIPTION OF THE DRAWINGS

The present invention will now be described in more detail with reference to the following Examples and the accompanying drawings in which:

FIG. 3 shows graphs obtained by dynamic light scattering (DLS) from dispersions prepared (a) by suspending Pigment Blue 15 obtained from the reactor according to one embodiment of the method of the present invention in deionised water and (b) a commercially available Pigment Blue 15 in deionised water;

DETAILED DESCRIPTION OF THE INVENTION

Figure 1:
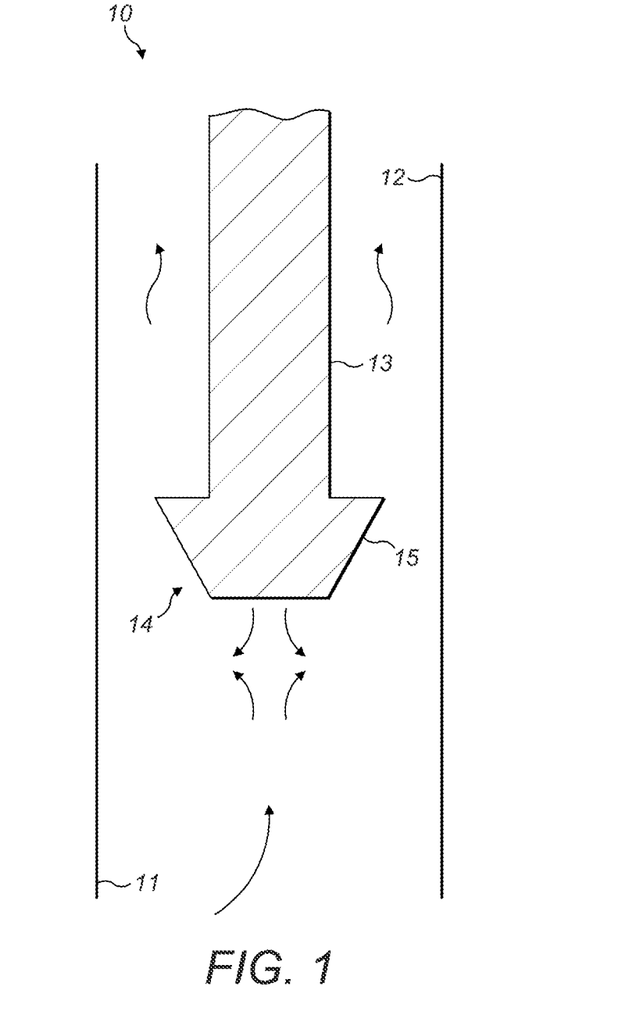
FIG. 1 is a schematic illustration of a counter current reactor, described in International Patent Application WO 2005/077505 A2, which is suitable for carrying out the method of the present invention.

Referring now to FIG. 1, a counter current mixing reactor, generally designated 10, comprises a first inlet 11 and an outlet 12 in which a second inlet 13 is diametrically opposed to the first inlet 11 and disposed in the first inlet 11. The first inlet 11 and the second inlet 13 are co-axial with one another and the second inlet 12 provides a nozzle 14 in the shape of a conical funnel 15.

Synthesis of Copper (II) Phthalocyanine (CuPC; Pigment Blue 15)

Figure 2:
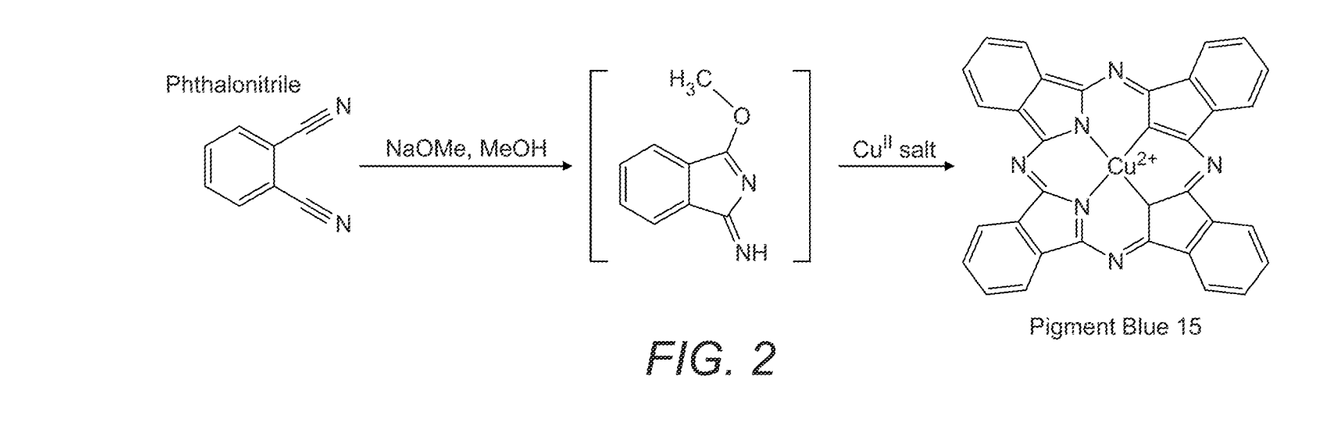
FIG. 2 is a scheme outlining the synthesis and dispersion of Pigment Blue 15 in the reactor of FIG. 1 according to one embodiment of the method of the present invention.

A proof-of-concept study examined the preparation of copper (II) phthalocyanine (Pigment Blue 15) by synthesis from the reactant precursors phthalonitrile and copper (II) nitrate hydrate (see FIG. 2) in a counter current mixing reactor as shown in FIG. 1 of laboratory scale.

In one experiment, an upward flow of a solution of copper (II) nitrate hydrate in methanol (0.03 M) and a downward flow of a solution of phthalonitrile in methanol (MeOH) containing sodium methoxide (NaOMe; 5 wt %) was arranged in the reactor using positive displacement pumps with 1:1 flow ratio at total (upward) flow rate 20 ml/min.

Prior to the mixing, the reactor was heated to a temperature of 200° C. and during the mixing the pressure within the reactor was maintained at 17.2 MPa using a back-pressure regulator.

The dark green to brown dispersion of copper (II) phthalocyanine exiting the reactor was collected and centrifuged to provide a dark blue pellet in yellow to green supernatant.

The pellet was removed from the supernatant, washed consecutively with water and tetrahydrofuran. After drying in an oven, a dark blue powder of copper (II) phthalocyanine (CuPC) was obtained.

Dispersions of the Synthesised Copper (II) Phthalocyanine

A dispersion of copper (II) phthalocyanine in water was prepared by the addition of deionised water containing a dispersant (Disperbyk 190) to the powder obtained above with stirring.

A sample was prepared from the dispersion for analysis by Dynamic Light Scattering (DLS) Spectroscopy by filtering through a 5.0 micron filter.

The filtered sample was analysed at 25° C. in a 10 mm cuvette using a Malvern Instruments Nano ZS particle sizer fitted with a back-scattering detector at 173° with an incident laser source (He—Ne laser with wavelength 632.8 nm).

A CONTIN algorithm was used to deconvolute the scattered light signal and give a size distribution. The analysis assumed a continuous phase of pure water (viscosity=0.8872 cP; refractive index=1.330) for the measurement settings. The z-average size of the nanoparticles was taken from the raw cumulants data fit from the DLS instrument.

Figure 3A:
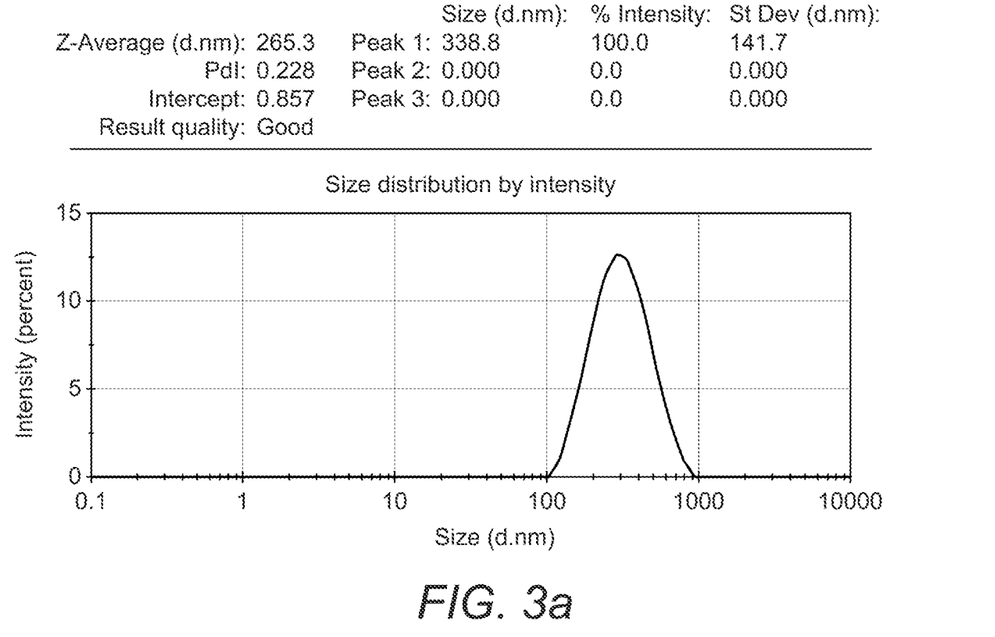
Figure 3B:
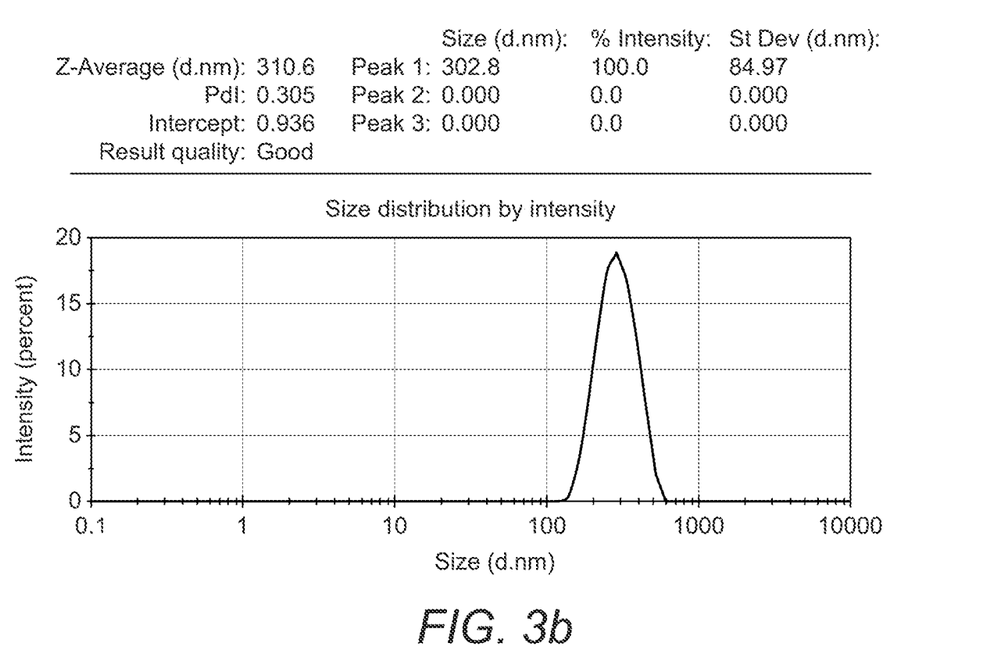

FIG. 3 shows the DLS spectrum (a) obtained for the dispersion and a DLS spectrum (b) obtained from a sample of a dispersion of commercially available Pigment blue 15 (Sigma-Aldrich) prepared in the same way.

As may be seen, the dispersions are unimodal and the Z-average (~median) particle size of the nanoparticles are respectively ~265 nm and ~310 nm. The DLS polydispersity index of each sample was determined as 0.228 and 0.305 respectively.

These dispersions, which are stable at standard room temperature and pressure, strongly suggest that dispersions of copper (II) phthalocyanine directly obtained from the reactor will be stable when a wetting agent and/or dispersant is present.

Infra-Red Spectrum of the Synthesised Copper (II) Phthalocyanine

An infra-red spectrum of the powder from the reactor was obtained by Fourier Transform Attenuated Total Reflectance (FT-ATR) infra-red spectrometry using a Perkin Elmer 100 FT-IR spectrometer equipped GRAMS/AI software. A diamond crystal was used and absorptions were recorded at a constant crystal pressure over 16 scans in the wavelength range 600 $cm^{-1}$ to 4000 $cm^{-1}$.

Figure 4:
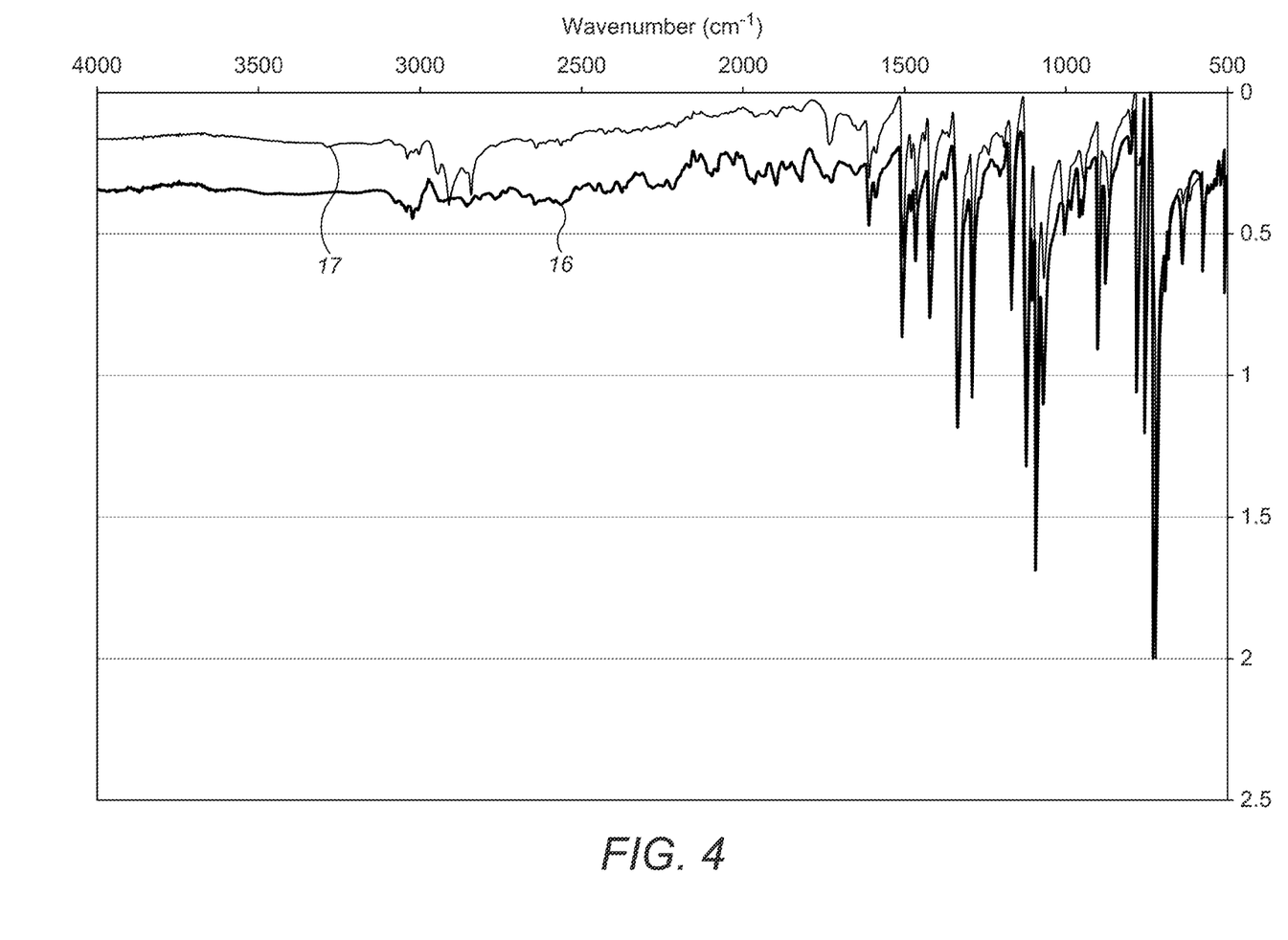
FIG. 4 shows FT-ATR infra-red spectra of Pigment Blue 15 obtained from the reactor according to one embodiment of the method of the present invention and a commercially available Pigment Blue 15.

The spectrum 17, shown in FIG. 4, is in excellent agreement (especially in the region from 500 $cm^{-1}$ to 1700 $cm^{-1}$) with an infra-red spectrum 16 obtained under similar conditions from commercially available Pigment blue 15 (Sigma-Aldrich).

Powder XRD Pattern of Synthesised Copper (II) Phthalocyanine

A powder X-ray diffraction (XRD) pattern was obtained from the powder using a Bruker AXS D8 X-ray diffractometer (Coventry, UK) with wavelength 0.154 nm, Cu source, voltage 40 kV and filament emission 40 mA. The 2θ scanning range was 5° to 90° and 0.02° steps were used at 1 second time counter. The scatter slit and the receiving slit were set at 0.2° and 0.1° respectively. Data were measured at room temperature in flat-plate geometry from powders pressed into a Macor ceramic holder. Data analysis was performed using the Philips incl. Diffraction Technology Traces software.

Figure 5:
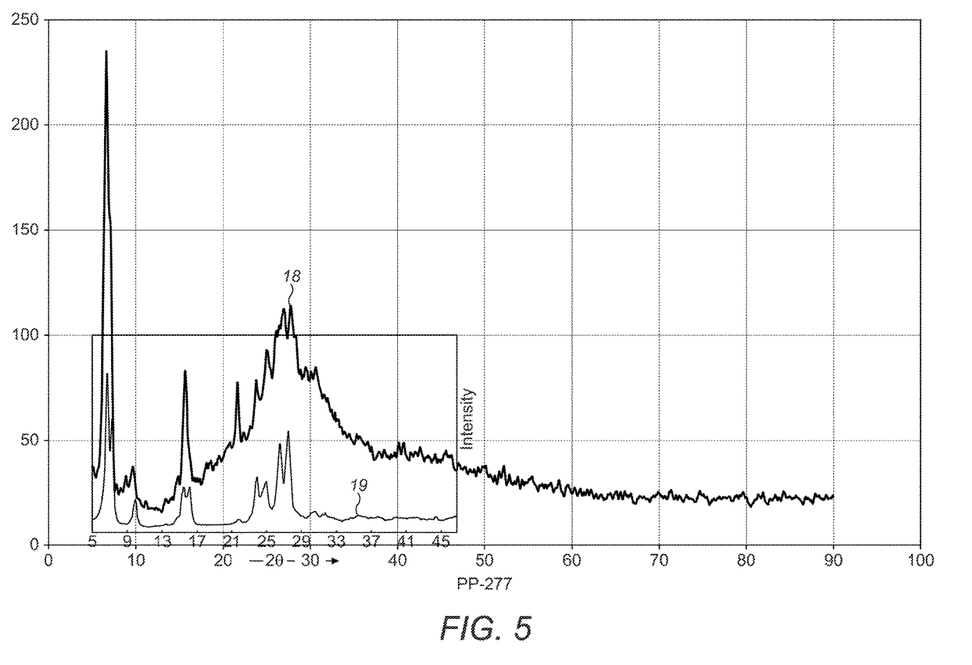
FIG. 5 is a powder X-ray diffraction pattern of the Pigment Blue 15 obtained from the reactor according to one embodiment of the method of the present invention.

FIG. 5 shows the X-ray diffraction pattern 18 obtained as compared to a library X-ray diffraction pattern 19 for the alpha polymorph of copper (II) phthalocyanine.

As may be seen, the pattern is in good agreement with the library pattern suggesting that the powder obtained from the reactor is predominantly crystalline and of the alpha form.

The presence of other peaks in the pattern suggests that the beta polymorph (and amorphous form) may also be present. It is envisaged, therefore, that selection in the parameters controlling nanoparticle size may also provide control over the crystalline form of the nanoparticles and, in particular, whether a single polymorph (alpha or beta) is obtained.

These studies clearly point to a method comprising tandem synthesis and precipitation of nanoparticle dispersions of a pigment in a counter current mixing reactor.

The size and polydispersity index of the dispersions are expected (on the basis of precipitation studies of disperse dyes described in our co-pending international patent application PCT/GB2018/053411) to be sensitive to, and controlled by, the selection of parameters such as ratio of flow rate of the organic solvent with the liquid carrier as well as selection of organic solvent and liquid carrier.

The present invention provides, therefore, a single, continuous process for the synthesis of stable dispersions of an organic pigment or an organic dye with desired nanoparticle size and encapsulation of the nanoparticles. It also provides a single, continuous process for the synthesis of solid organic compounds with desired nanoparticle size.

The processes are suitable for large scale production and environmentally responsible because they avoid the need for the large amounts of energy and solvent that are necessary for large scale milling.

The present invention may also allow the preparation of nanoparticle dispersions or nanoparticles of organic dyes or pigments which cannot be milled effectively (for example, Disperse Red 55). It may, therefore, provide access to stable dispersions of solid organic dyes or pigments which are not presently obtainable. It may further provide access to new polymorphs of the crystalline organic dyes or pigments.

Note that the nanoparticle diameters specified herein are references to diameters which may be determined by, or calculated from, DLS or the dispersions in accordance with ISO 22412:2017. The solid contents specified herein are references to solid contents which may be determined by drying in accordance with ISO 3251:2008.

Note also that the nanoparticles of the present invention are not comprised or reliant on an oil-in-water emulsion but are instead comprised by the solid organic dye or pigment or by the solid organic dye or pigment encapsulated (at least in part) by a water soluble surfactant.

Note further that the methods of the present invention may find general applicability to the preparation of nanoparticle dispersions and nanoparticles of other solid organic compounds including pharmaceutical actives, pharmaceutical additives, pharmaceutical excipients, organometallic dopants or emitters useful in organic light emitting diodes (OLEDs) and organometallic catalysts useful in catalytic convertors and in organic synthesis.

The invention claimed is:

1. A method for preparing a dispersion of nanoparticles, the method comprising:
   providing:
      a solid organic dye or pigment in a liquid carrier;
      a first solution or slurry comprising a reactant precursor for the solid organic dye or pigment in an organic or other solvent;
      a counter current or concurrent mixing reactor comprising a first inlet for at least the first solution or slurry, a second inlet for at least the solid inorganic dye or pigment in the liquid carrier, and an outlet; wherein the second inlet is co-axially disposed with and/or diametrically opposed to the first inlet;
   continuously mixing the first solution or slurry with the solid organic dye or pigment in the liquid carrier within the counter current or concurrent mixing reactor at a pressure of 10 MPa to 25 MPa and a temperature of 100° ° C.to 250° C., wherein the first solution or slurry is fed through the first inlet and the solid organic dye or pigment in the liquid carrier is fed through the second inlet, whereby to obtain reaction of the reactant precursor with the solid organic dye or pigment and formation of the solid organic dye or pigment as a dispersion of nanoparticles in the liquid carrier and solvent mixture;
      wherein the first solution or slurry and/or the solid organic dye or pigment in the liquid carrier have a residence time of between 1 second and 5 minutes;
   optionally, removing unreacted reactant precursor and/or by-product from the dispersion of nanoparticles when present; and
   optionally, concentrating the dispersion of nanoparticles.

2. A method according to claim 1, wherein the first solution or slurry and/or the liquid carrier contains a wetting agent and/or a dispersant.

3. A method according to claim 1, further comprising adding a wetting agent and/or a dispersant to the dispersion of nanoparticles.

4. A method according to claim 1, wherein the dispersion of nanoparticles has a median (Z) diameter between 100 nm to 300 nm.

5. A method according to claim 4, wherein the dispersion of nanoparticles has a unimodal polydispersity.

6. A method according to claim 5, wherein the dispersion of nanoparticles has a solid content greater than 5.0 wt/wt % and less than 15 wt/wt %.

7. A method according to claim 6, wherein the dispersion of nanoparticles has a dynamic light scattering (DLS) polydispersity index between 0.1 and 3.0.

8. A method according to claim 1, wherein the method comprises controlling one or more of nanoparticle size and/or polydispersity by selection of the organic or other solvent in the first solution, the liquid carrier, a concentration of reactant precursors in the first solution or slurry, the temperature, the pressure, the residence times of the first solution or slurry and/or the solid inorganic dye or pigment in the liquid carrier, and/or a ratio of flow rates of the first solution or slurry and the solid inorganic dye or pigment in the liquid carrier in the counter current or concurrent mixing reactor.

9. A method according to claim 7, wherein the liquid carrier comprises water.

10. A method according to claim 9, wherein the organic solvent is one or more of ethyl acetate, ethanol, methanol, diethyl ether, tetrahydrofuran, dimethylformamide, dimethyl sulfoxide, N-methyl-2-pyrrolidone, acetone, ethylene glycol, propylene glycol and isopropyl alcohol.

* * * * *